United States Patent [19]

Ikada et al.

[11] Patent Number: 4,988,761

[45] Date of Patent: Jan. 29, 1991

[54] PROCESS FOR PRODUCING A LOW WATER CONTENT PVA HYDROGEL

[75] Inventors: Yoshito Ikada; Shokyu Gen, both of Uji, Japan

[73] Assignees: Dow Corning K.K., Tokyo; Bio-Materials Univers Co., Kyoto; Kyocera Corp., Kyota, all of Japan

[21] Appl. No.: 343,468

[22] Filed: Apr. 26, 1989

[30] Foreign Application Priority Data

Sep. 22, 1988 [JP] Japan .................................. 63-236572

[51] Int. Cl.$^5$ .............................................. C08L 29/04
[52] U.S. Cl. ....................................... 524/557; 525/61
[58] Field of Search ........................... 524/557; 525/61

[56] References Cited

U.S. PATENT DOCUMENTS

| 4,663,358 | 5/1987 | Hyon et al. | 521/64 |
| 4,734,097 | 3/1988 | Tanabe et al. | 623/11 |
| 4,808,353 | 2/1989 | Nambu et al. | 264/28 |

OTHER PUBLICATIONS

Hydrogels in Medicine and Pharmacy, vol. III, Properties and Applications, Nikolaos A. Peppas, Professor, CRC Press, Inc., Boca Raton, FL.

*Primary Examiner*—Joseph L. Schofer
*Assistant Examiner*—J. M. Reddick
*Attorney, Agent, or Firm*—Allen O. Maki

[57] ABSTRACT

The present invention relates to a method of producing polyvinyl alcohol hydrogel characterized by the following features: the production process consists of a low-temperature processing stage in which the solution of polyvinyl alcohol with a polymerization degree over 1200 is processed at a low temperature so that polyvinyl alcohol is gelated, and a high-temperature processing stage in which the polyvinyl alcohol gelated int he low-temperature processing stage is dried, then processed at higher than 100° C.; in this way, polyvinyl alcohol hydrogel with a saturated water content lower than 40 wt % is obtained. The hydrogels of this invention are useful for providing improved artificial articular cartilage for replacement of cartilage in the human body.

7 Claims, No Drawings

PROCESS FOR PRODUCING A LOW WATER CONTENT PVA HYDROGEL

The present invention relates to a method of producing polyvinyl alcohol hydrogel characterized by the following features: the production process consists of a low-temperature processing stage in which the solution of polyvinyl alcohol with a polymerization degree over 1200 processed at a low temperature so that polyvinyl alcohol is gelated, and a high-temperature processing stage in which the polyvinyl alcohol gelated in the low-temperature processing stage is dried, then processed at higher than 100° C.; in this way, polyvinyl alcohol hydrogel with a saturated water content lower than 40 wt % is obtained. The hydrogels of this invention are useful for providing improved artificial articular cartilage for replacement of cartilage in the human body.

DETAILED DESCRIPTION OF THE INVENTION

This invention concerns a method of producing polyvinyl alcohol (referred to as "PVA" hereafter) hydrogel. In particular, it concerns a production method for PVA hydrogels with a low saturated water content.

CONVENTIONAL TECHNIQUES

PVA is a typical water-soluble polymer and can form a hydrogel. The PVA hydrogel has excellent compatibility with organisms and other good properties; hence, it is being used as a starting material to make artificial cartilage, etc. However, since PVA hydrogel usually has a low mechanical strength, its application field is quite limited.

A conventional procedure proposed to increase the mechanical strength of the PVA hydrogel involves the introduction of a crosslinked structure into the hydrogel. However, the specific method to implement this scheme is rather complicated, and is difficult to implement in industry. Besides, by the introduction of the crosslinked structures, the excellent properties of the PVA hydrogel may be degraded.

With this technical background, a gelation process has recently been developed to accelerate the crystallization by treating PVA at a low temperature. Using this technique, the so-called pure PVA hydrogel acquires an improved mechanical strength.

However, when the gelation process is performed using this low temperature processing technique, the obtained PVA hydrogel has a high water content and hence unstable properties. As a result, although the PVA hydrogel has several excellent properties, its mechanical strength is still insufficient.

One process for producing biologically compatible materials from PVA hydrogels is disclosed in U.S. Pat. No. 4,808,353 (Nambu, et al.) issued Feb. 28, 1989. In the procedure described therein the hydrogel is subjected to a freezing step at a temperature below $-30°$ C. and then thawing at a temperature below 55° C. The steps are repeated to obtain a material with a degree of hydrolysis over 95 mol %. This process and resulting material both thus differ significantly from those of this invention.

The purpose of this invention is to solve the problems encountered previously by providing a reliable method of PVA hydrogel production which provides a hydrogel with high mechanical strength and stable characteristics.

This invention provides a method for production of PVA hydrogel characterized by the following features: the production process consists of a low-temperature processing stage in which the solution of polyvinyl alcohol with a polymerization degree of over 1200 is processed at a low temperature so that polyvinyl alcohol is gelated, and a high-temperature processing stage in which the polyvinyl alcohol gelated in the low-temperature processing stage is dried, then processed at higher than 100° C.; in this way, polyvinyl alcohol hydrogel with a saturated water content lower than 40 wt % is obtained.

Using the method of this invention, PVA hydrogel with a low saturated water content, a high mechanical strength, and stable characteristics can be produced in a reliable way.

DETAILED DESCRIPTION

According to this invention, the PVA solution prepared beforehand is cooled to lower than room temperature or preferably lower than 0° C., which constitutes a low-temperature treatment to accelerate crystallization of PVA for gelation. The gelated PVA is then fully dehydrated and dried; afterwards, the sample is heated to higher than 100° C. for high-temperature treatment. In this way, PVA hydrogel with a saturated water content lower than 40 wt % can be obtained.

According to this invention, the species of PVA used should have an average polymerization degree higher than 1200, or preferably higher than 1500, or higher than 1700 with even better results. If the PVA species used has an average polymerization degree lower than 1200, the finally obtained PVA hydrogel may not have sufficient mechanical strength. In addition, the PVA species used should have a saponification degree higher than 95 mol %.

As far as the solvent used to prepare the PVA solution is concerned, it is preferred that a mixture solvent made of water and a water-miscible organic solvent be used. The species of the water-miscible organic solvents include dimethyl sulfoxide, dimethylformamide, formaldehyde, acetaldehyde, ethylene oxide, methyl acetate, N-methylacetamide, dimethoxymethane, methyl ethyl ketone, 1,1-dimethoxyethane, phenol, aniline, 1,3-dimethyl-2-imidazolidinone, as well as low-molecular-weight alcohols such as methyl alcohol, ethyl alcohol, propyl alcohol, ethylene glycol, propylene glycol, triethylene glycol, glycerin, etc.

The proportions of water and organic solvent of the solvent mixture can be arbitrarily selected, as long as this mixture can fully dissolve PVA in the heated state. Usually, the proportional ratio of water to the organic solvent for the solvent mixture should be 5:95 to 30:70.

There is no special limitation on the concentration of PVA in the PVA solution. This concentration can be selected according to the desired properties of the final product of PVA hydrolyzed. However, it usually should be 1 to 30 wt %.

There is no special limitation on the method used to prepare the PVA solution. For example, a preferable process is as follows: an appropriate amount of PVA is mixed with a solvent to obtain a suitable concentration, the mixture is then heated to 100 to 120° C. to fully dissolve PVA in it.

Afterwards, the PVA solution is cooled and treated at a low temperature. This low-temperature treatment is usually performed by cooling the system to below 0° C., for instance as low as −20° C. or lower. In this low-temperature treatment, the crystallization is accelerated in PVA.

The gelated PVA sample obtained in this way contains a lot of water. It should then be dried. The drying treatment ma be performed using any of the following methods: air drying, heat drying, vacuum dehydration, etc. It is preferred that this drying treatment be performed to a high degree, for example, until the water content of the gelated PVA becomes lower than 3 wt %. Hence, it is appropriate to make use of several drying treatment methods in combination. For example, after the primary drying state using air drying and heat drying, a secondary drying is performed using vacuum dehydration. If the drying degree is not sufficient in this drying treatment, the effect of a high-temperature treatment in the later process will not be sufficiently obtained.

The dried gelated PVA is then processed at a high temperature. The high-temperature treatment is performed by heating the related PVA to higher than 100° C. Although the high-temperature treatment can be performed in air, in order to prevent oxidation decomposition, it is preferred that this treatment be performed in vacuum, in an inactive gas (nitrogen, etc.) stream, or in an inactive medium such as silicone oil. The heating temperatures should be higher than 100° C. It should be lower than about 200° C. in consideration of the melting point of PVA. Preferably, the temperature should be 120 to 160° C. The high-temperature processing time depends on the drying degree of PVA and the high-temperature processing temperature. Usually, it should be 5 minutes to 10 hours, or preferably 10 minutes to 5 hours. When the high-temperature processing temperature is higher or the processing time is longer, the obtained PVA hydrogel will have a lower saturated water content.

After the above-mentioned processing stages, PVA hydrogel with a saturated water content lower than 40 wt % can be produced. Here, the so-called "saturated water content" refers to the proportion by weight of water contained in the hydrogel sample after it is immersed in a large amount of water at room temperature until the saturated state is reached.

The PVA hydrogel produced in this way has a saturated water content less than 40 wt % and has improved mechanical strength. If the saturated water content is higher than 40 wt %, sufficient mechanical strength cannot be obtained.

It is not yet fully clarified with regard to the mechanism for the excellent effects of the PVA hydrogel prepared using the method of this invention. However, it is estimated that for the PVA sample related in the low-temperature treatment to the extent the there is almost no water contained in it, and then subjecting it to the high-temperature treatment, the gelated PVA acquires a finer crystalline structure. As a result, the swelling property with respect to water is decreased. Hence, a low saturated water content and a high mechanical strength can be realized.

According to the method of this invention, PVA hydrolyzed with a low saturated water content and a high mechanical strength can be produced in a reliable way. In addition, the obtained PVA hydrogel has stable properties.

Since the PVA hydrogel produced using the method of this invention has a high mechanical strength, it can be used to make artificial cartilage using its compatibility with organisms. Besides, it may be used in various other applications using its other properties.

EXAMPLES

In the following, this invention will be explained with reference to the following examples, however, the invention is not intended to be limited thereby.

EXAMPLE 1

PVA (product of Unichika K.K.) with a polymerization degree of 4800 and a saponification degree of 99.5 mol % was dissolved at 12° C. in a mixture solvent made of dimethyl sulfoxide and water at a weight ratio of 80:20. The solution was heated for 2 hours to ensure a full dissolution, forming a transparent solution with a PVA concentration of 15 wt %. This solution was then slowly stirred until it was cooled to room temperature. The viscosity of the solution increased as the temperature decreased. The obtained sticky solution was poured into a test tube of an appropriate size. After leaving undisturbed for 24 hours at −° C. for a low-temperature treatment for gelation, the gelated PVA sample was dried for 24 hours in a dry air atmosphere, followed by dehydration for 3 hours using a vacuum dehydrating machine. Afterwards, the dried PVA gel was processed for high-temperature treatment in a silicone oil bath kept at a constant temperature of 120° C. for 1 hour.

The obtained PVA hydrogel sample was placed in a large amount of water for 3 days until the equilibrium state was reached. The saturated water content was then measured and was found to be 38 wt %.

A 4 mm thick sample was prepared by slicing the obtained PVA hydrogel sample. A thruster with a weight of 3.7 kg was made to fall from a height of 10 mm on the sample; the load waveform of the sample was measured on a digital analyzer with the aid of a load cell. The results show that the PVA hydrogel has excellent impact absorptivity and a high mechanical strength.

EXAMPLES 2 & 3

Two species of PVA hydrogel were produced in the same way as in Example 1 except that the temperature of the constant-temperature bath was changed to 140° C. and 160° C., respectively. The obtained species of PVA hydrogel had saturated water contents of 28 wt % and 20 wt %, respectively.

For these species of PVA hydrogel, the same test as in Example 1 was performed. The results indicated that they have the same excellent mechanical properties.

EXAMPLE 4

In the same way as in Example 1, a transparent solution with a PVA concentration of 15 wt % was prepared. The solution was slowly stirred and cooled to room temperature. As the temperature decreased, the viscosity of the liquid increased. The obtained sticky liquid was spread between a pair of flat glass sheets to form a film. After the film was left at −5° C. for 24 hours, it was dried in the same way as in Example 1. A high-temperature treatment was then performed at 100° C. to form the film-shaped PVA hydrogel. The obtained PVA hydrogel had a saturated water content of 37 wt %.

The tensile strength of the PVA hydrogel was measured. It was found that the stress was 10 MPa when the elongation was 200%. This indicated that the PVA hydrogel had a high mechanical strength.

EXAMPLES 5 & 6

Two species of PVA hydrogel film were produced in the same way as in Example 4 except that the temperature of the constant-temperature bath for the high-temperature treatment was changed to 120° C. and 140° C., respectively. The saturated water contents of these species of PVA hydrogel were found to be 23 wt % and 20 wt%, respectively.

For these species of PVA hydrogel, the same test as in Example 4 was performed. The stress at an elongation of 200% was found to be 18 MPa and 20 MPa, respectively, indicating that they had excellent mechanical properties.

That which is claimed is:

1. A process of producing polyvinyl alcohol hydrogel comprising (A) subjecting a solution in a mixture of water and water-miscible organic solvent of polyvinyl alcohol with a polymerization degree over 1200, to a temperature below −5° C. so that the polyvinyl alcohol is gelated, (B) drying said hydrogel at an elevated temperature so that it contains less than about 3% by weight of water, (C) subjecting said hydrogel to a temperature higher than 100° C. for a time sufficient to reduce the size of the PVA crystals in said hydrogel, (D) saturating the resulting hydrogel with water, whereby polyvinyl alcohol hydrogel with a saturated water content lower than 40 wt % is obtained.

2. A process according to claim 1 wherein said PVA has a degree of saponification higher than 95 mol %.

3. A process according to claim 1 wherein said polyvinyl alcohol has an average degree of polymerization over 1500.

4. A process according to claim 1 wherein the ratio of water to organic solvent is between 5:95 and 30:70.

5. A process according to claim 1 wherein said hydrogel is dried to a water content of less than 3% by weight.

6. A process according to claim 1 wherein said heating step is carried out in a vacuum, an inert gas, or an inert liquid.

7. A process according to claim 6 wherein said heating step is carried out between 120° C. and 160° C.

* * * * *